United States Patent
Lee et al.

(10) Patent No.: US 9,401,018 B2
(45) Date of Patent: Jul. 26, 2016

(54) ULTRASONIC DIAGNOSTIC APPARATUS AND METHOD FOR ACQUIRING A MEASUREMENT VALUE OF A ROI

(71) Applicant: SAMSUNG MEDISON CO., LTD., Gangwon-Do (KR)

(72) Inventors: Jun-kyo Lee, Gangwon-Do (KR); Chul-an Kim, Gangwon-Do (KR); Jae-moon Jo, Gangwon-Do (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 60 days.

(21) Appl. No.: 14/312,013

(22) Filed: Jun. 23, 2014

(65) Prior Publication Data

US 2014/0376793 A1     Dec. 25, 2014

(30) Foreign Application Priority Data

Jun. 25, 2013   (KR) .................. 10-2013-0073319

(51) Int. Cl.
| | |
|---|---|
| *G06K 9/00* | (2006.01) |
| *G06T 7/00* | (2006.01) |
| *A61B 8/00* | (2006.01) |
| *A61B 8/08* | (2006.01) |
| *G01S 7/52* | (2006.01) |
| *A61B 5/0205* | (2006.01) |

(Continued)

(52) U.S. Cl.
CPC ............... *G06T 7/0012* (2013.01); *A61B 8/463* (2013.01); *A61B 8/465* (2013.01); *A61B 8/469* (2013.01); *A61B 8/5215* (2013.01); *G01S 7/52063* (2013.01); *G01S 7/52073* (2013.01); *G01S 7/52074* (2013.01); *A61B 5/0205* (2013.01); *A61B 5/055* (2013.01); *A61B 5/748* (2013.01); *A61B 8/4427* (2013.01); *A61B 8/466* (2013.01)

(58) Field of Classification Search
None
See application file for complete search history.

(56) References Cited

U.S. PATENT DOCUMENTS

| | | | |
|---|---|---|---|
| 5,471,989 A | 12/1995 | Roundhill et al. | |
| 6,217,517 B1 | 4/2001 | Grunwald | |

(Continued)

FOREIGN PATENT DOCUMENTS

| | | | |
|---|---|---|---|
| JP | 09-131342 A | 5/1997 | |
| JP | 10-314167 A | 12/1998 | |

(Continued)

OTHER PUBLICATIONS

Korean Notice of Allowance mailed on Mar. 31, 2015, issued in corresponding Korean Patent Application No. 10-2013-0073319; 7 pages with English translation.

(Continued)

*Primary Examiner* — Tahmina Ansari
(74) *Attorney, Agent, or Firm* — McDermott Will & Emery LLP

(57) ABSTRACT

Provided are an ultrasonic diagnostic apparatus and a method of operating the same. A method of operating the ultrasonic diagnostic apparatus includes displaying an ultrasonic image in a first region of a display unit, selecting a region of interest (ROI) in the ultrasonic image, displaying a scan conversion image and a certain magnification in a second region, and acquiring a measurement value of the ROI on a basis of the scan conversion image. The scan conversion image is generated by enlarging or reducing an image corresponding to the selected ROI at the certain magnification. A resolution of the scan conversion image is equal to or higher than a resolution of the ultrasonic image.

17 Claims, 11 Drawing Sheets

(51) Int. Cl.
*A61B 5/055* (2006.01)
*A61B 5/00* (2006.01)

(56) References Cited

U.S. PATENT DOCUMENTS

| | | |
|---|---|---|
| 6,413,217 B1 | 7/2002 | Mo |
| 6,803,931 B1 | 10/2004 | Roman et al. |
| 7,346,199 B2 * | 3/2008 | Pfaff ................ G06T 19/00 382/128 |
| 2006/0289752 A1 * | 12/2006 | Fukunishi ............ H01J 37/28 250/310 |
| 2008/0063305 A1 | 3/2008 | Lim |
| 2009/0299181 A1 | 12/2009 | Ito et al. |
| 2011/0043434 A1 | 2/2011 | Roncalez et al. |
| 2012/0130244 A1 | 5/2012 | Kim |
| 2013/0011028 A1 * | 1/2013 | Marugame ............ G06T 3/40 382/128 |
| 2014/0376793 A1 * | 12/2014 | Lee ................ G06T 7/0012 382/131 |

FOREIGN PATENT DOCUMENTS

| | | |
|---|---|---|
| JP | 2009-285051 A | 12/2009 |
| JP | 2011-239906 A | 12/2011 |
| KR | 10-2012-0053626 A | 5/2012 |

OTHER PUBLICATIONS

Korean Office Action issued in corresponding Korean Application No. 10-2013-0073319, dated Aug. 5, 2014, with English translation.
Extended European Search Report issued in corresponding European Application No. 14160489.2, dated Aug. 5, 2014.

* cited by examiner

ULTRASONIC DIAGNOSTIC APPARATUS AND METHOD FOR ACQUIRING A MEASUREMENT VALUE OF A ROI

CROSS-REFERENCE TO RELATED PATENT APPLICATION

This application claims the benefit of Korean Patent Application No. 10-2013-0073319, filed on Jun. 25, 2013, in the Korean Intellectual Property Office, the disclosure of which is incorporated herein in its entirety by reference.

BACKGROUND OF THE INVENTION

1. Field of the Invention

The present invention relates to an ultrasonic diagnostic apparatus and a method of operating the same, and more particularly, to an ultrasonic diagnostic apparatus and a method of operating the same for increasing the accuracy of numerical value measurement of an object of interest.

2. Description of the Related Art

Ultrasonic diagnostic apparatuses irradiate an ultrasonic signal, generated from a transducer of a probe, onto a target object and receive information of an echo signal reflected from the object, thereby obtaining an image of an internal part of the object. In particular, the ultrasonic diagnostic apparatuses are used for the medical purpose of observing the inside of a target object, detecting a foreign material, and measuring an injury. Ultrasonic diagnostic apparatuses have a higher stability than diagnostic apparatuses using X-rays, display an image in real time, and are safe because there is no exposure to radioactivity, and thus are widely used along with another image diagnostic apparatus.

An ultrasonic diagnostic apparatus selects a boundary or specific point of an object of interest (OOI) displayed on an ultrasonic image, for diagnosing an internal OOI of a target object, and measures a distance or area of the OOI.

In this case, when the OOI is insufficiently displayed or the boundary or the like of the OOI is not clearly displayed, it is difficult to select a point or a region to be measured, and for this reason, accuracy of measurement is reduced.

SUMMARY OF THE INVENTION

The present invention provides an ultrasonic diagnostic apparatus and a method of operating the same, which provide a scan conversion image enabling a user to accurately select a measurement point of an object of interest (OOI), thus increasing accuracy of measurement of the OOI.

According to an aspect of the present invention, there is provided a method of operating an ultrasonic diagnostic apparatus, including: displaying an ultrasonic image in a first region of a display unit; selecting a region of interest (ROI) in the ultrasonic image; displaying a scan conversion image and a certain magnification in a second region, wherein the scan conversion image is generated by enlarging or reducing an image corresponding to the selected ROI at the certain magnification; and acquiring a measurement value of the ROI on a basis of the scan conversion image, wherein resolution of the scan conversion image is equal to or higher than resolution of the ultrasonic image.

The selecting of an ROI may include selecting the ROI on a basis of a user input, wherein the user input includes at least one of an input for selecting a certain region in the ultrasonic image, an input of a coordinate value of the certain region, and an input for selecting a specific object included in the ultrasonic image.

The acquiring of a measurement value may include acquiring at least one measurement value of a distance, area, angle, and volume of an object of interest included in the ROI.

The method may further include displaying the measurement value.

The certain magnification may include a first magnification and a second magnification, and the displaying of a scan conversion image may include displaying a first scan conversion image scan-converted at the first magnification and a second scan conversion image scan-converted at the second magnification.

The method may further include displaying a first measurement value acquired on a basis of the first scan conversion image, a second measurement value acquired on a basis of the second scan conversion image, and a third value calculated on a basis of the first and second measurement values.

The displaying of a scan conversion image may include: detecting an edge of an OOI included in the ROI on a basis of image data corresponding to the ROI; and displaying the detected edge of the OOI in the scan conversion image.

The detecting of an edge may include detecting the edge of the OOI on a basis of first and second edge detection techniques.

The displaying of a scan conversion image may include displaying a first edge detection image, in which a first edge detected by the first edge detection technique is displayed in the scan conversion image, and a second edge detection image in which a second edge detected by the second edge detection technique is displayed in the scan conversion image.

According to another aspect of the present invention, there is provided an ultrasonic diagnostic apparatus include: a user input unit that receives a user input for selecting an ROI in an ultrasonic image; an image processor that performs a scan conversion which enlarges or reduces an image, corresponding to the ROI selected by the user input, at the certain magnification; a display unit that displays the scan-converted scan conversion image and a certain magnification; and a controller that acquires a measurement value of the ROI on a basis of the scan conversion image, wherein resolution of the scan-converted image is equal to or higher than resolution of the ultrasonic image.

The user input unit may receive at least one of an input for selecting a certain region in the ultrasonic image, an input of a coordinate value of the certain region, and an input for selecting a specific object included in the ultrasonic image.

The controller may acquire at least one measurement value of a distance, area, angle, and volume of an object of interest included in the ROI.

The display unit may display the measurement value.

The certain magnification may include a first magnification and a second magnification, and the display unit may display a first scan conversion image scan-converted at the first magnification and a second scan conversion image scan-converted at the second magnification.

The display unit may display a first measurement value acquired on a basis of the first scan conversion image, a second measurement value acquired on a basis of the second scan conversion image, and a third value calculated on a basis of the first and second measurement values.

The ultrasonic diagnostic apparatus may further include an edge detection unit that detects an edge of an OOI included in the ROI on a basis of image data corresponding to the ROI, wherein the scan conversion image includes the detected edge.

The edge detection unit may detect the edge of the OOI on a basis of first and second edge detection techniques.

The display unit may display a first edge detection image, in which a first edge detected by the first edge detection technique is displayed in the scan conversion image, and a second edge detection image in which a second edge detected by the second edge detection technique is displayed in the scan conversion image.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
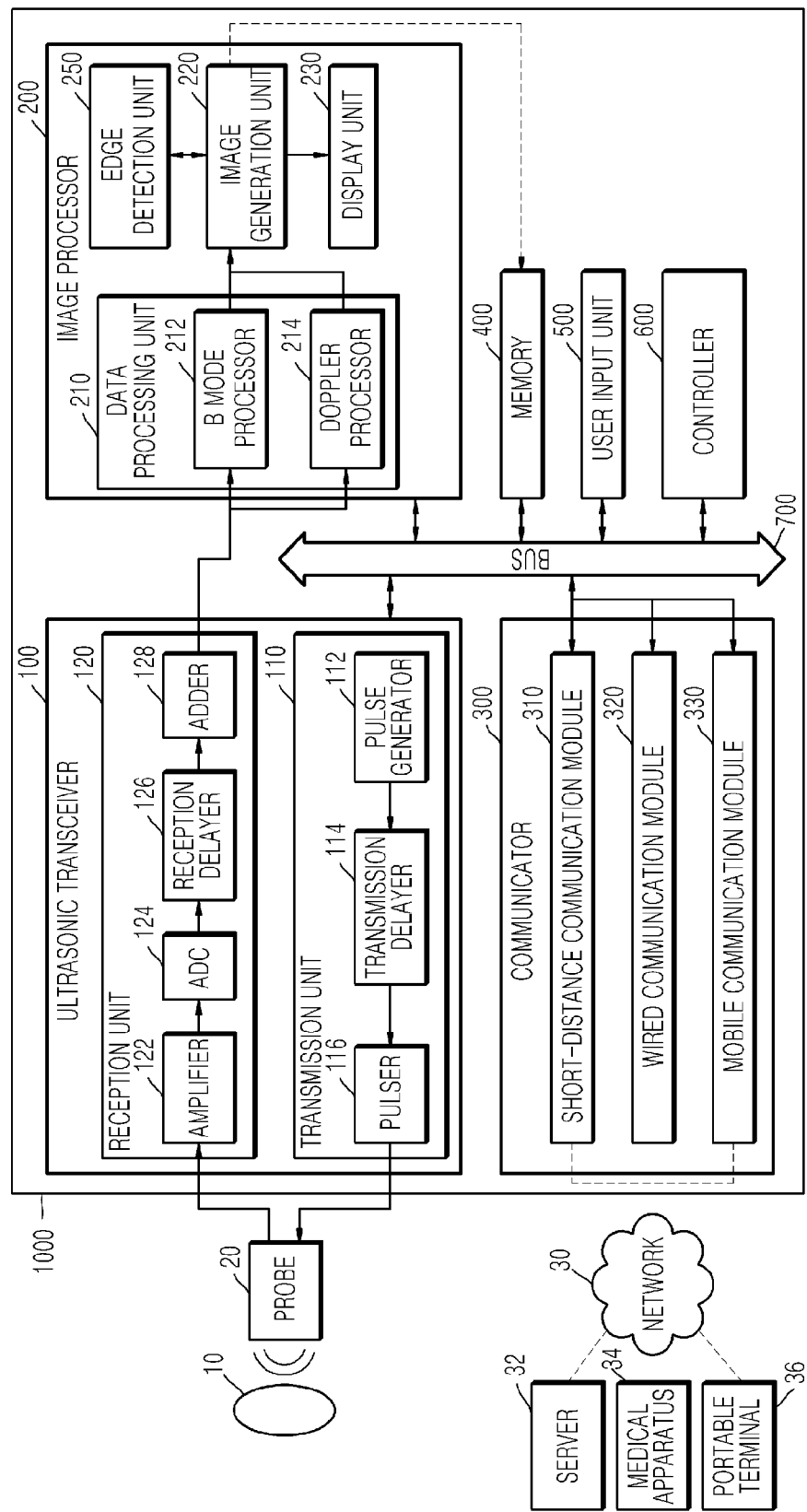
FIG. 1 is a block diagram illustrating a configuration of an ultrasonic diagnostic apparatus according to an embodiment of the present invention.

All terms including descriptive or technical terms which are used herein should be construed as having meanings that are obvious to one of ordinary skill in the art. However, the terms may have different meanings according to an intention of one of ordinary skill in the art, precedent cases, or the appearance of new technologies. Also, some terms may be arbitrarily selected by the applicant, and in this case, the meaning of the selected terms will be described in detail in the detailed description of the invention. Thus, the terms used herein have to be defined based on the meaning of the terms together with the description throughout the specification.

Also, when a part "includes" or "comprises" an element, unless there is a particular description contrary thereto, the part may further include other elements, not excluding the other elements. Moreover, each of terms such as " . . . unit" and "module" described in specification denotes an element for performing at least one function or operation, and may be implemented in hardware, software or a combination of hardware and software.

The term "ultrasonic image" used herein denotes an image of a target object acquired by using an ultrasonic wave. Also, the term "target object" used herein may include a person, an animal, a part of the person, or a part of the animal. For example, an object may include an organ such as a liver, a heart, a womb, a brain, breasts, an abdomen, or the like, or a blood vessel. Also, the term "object" may include a phantom. The phantom denotes a material having a volume that is very close to a density and effective atomic number of an organism, and may include a spherical phantom having a characteristic similar to a physical body.

Moreover, the ultrasonic image may be implemented in various ways. For example, the ultrasonic image may be at least one of an amplitude (A) mode image, a brightness (B) mode image, a color (C) mode image, and a Doppler (D) mode image. Also, according to an embodiment of the present invention, the ultrasonic image may be a two-dimensional (2D) image or a three-dimensional (3D) image.

Moreover, the "user" used herein is a medical expert, and may be a doctor, a nurse, a medical technologist, a medical image expert, or the like, or may be an engineer repairing a medical apparatus. However, the user is not limited thereto.

The present invention will now be described more fully with reference to the accompanying drawings, in which exemplary embodiments of the invention are shown. The invention may, however, be embodied in many different forms and should not be construed as being limited to the embodiments set forth herein; rather, these embodiments are provided so that this disclosure will be thorough and complete, and will fully convey the concept of the invention to those of ordinary skill in the art. In the following description, well-known functions or constructions are not described in detail since they would obscure the invention with unnecessary detail. Throughout the specification, like reference numerals in the drawings denote like elements.

FIG. 1 is a block diagram illustrating a configuration of an ultrasonic diagnostic apparatus 1000 according to an embodiment of the present invention. The ultrasonic diagnostic apparatus 1000 according to an embodiment of the present invention includes a probe 20, an ultrasonic transceiver 100, an image processor 200, a communicator 300, a memory 400, a user input unit 500, and a controller 600. The above-described elements may be connected to each other through a bus 700.

The ultrasonic diagnostic apparatus 1000 may be implemented as a portable type as well as a card type. Examples of the portable diagnostic apparatuses may include picture archiving and communication system (PACS) viewers, smartphones, laptop computers, personal digital assistants (PDAs), tablet personal computers (PCs), etc., but are not limited thereto.

The probe 20 irradiates an ultrasonic signal onto a target object 10 according to a driving signal applied from the ultrasonic transceiver 100, and receives an echo signal reflected from the target object 10. The probe 20 includes a plurality of transducers, which vibrate according to the applied driving signal to generate an ultrasonic wave that is sound energy. Also, the probe 20 may be connected to a body of the ultrasonic diagnostic apparatus 1000 in a wired or wireless manner, and the ultrasonic diagnostic apparatus 1000 may include a plurality of the probes 20 depending on an implementation type.

A transmission unit 110 supplies the driving signal to the probe 20, and includes a pulse generator 112, a transmission delayer 114, and a pulser 116. The pulse generator 112 generates a pulse used to generate a transmission ultrasonic wave based on a pulse repetition frequency (PRF), and the transmission delayer 114 applies a delay time, used to determine a transmission directionality, to the pulse. A plurality of the pulses with the delay directionality applied thereto correspond to a plurality of piezoelectric vibrators included in the probe, respectively. The pulser 116 applies the driving signal (or a driving pulse) to the probe 20 at a timing corresponding to each of the pulses with the delay time applied thereto.

The reception unit 120 processes the echo signal received from the probe 20 to generate ultrasonic data, and includes an amplifier 122, an analog-to-digital converter (ADC) 124, a reception delayer 126, and an adder 128. The amplifier 122 amplifies the echo signal for each channel, and the ADC 124 converts the amplified echo signal from analog to digital. The reception delayer 126 applies a delay time, used to determine a reception directionality, to the digital-converted echo signal, and the adder 128 adds a plurality of the echo signals processed by the reception delayer 166 to generate the ultrasonic data.

The image processor 200 performs a scan conversion on the ultrasonic data generated by the ultrasonic transceiver 100 to generate and display an ultrasonic image.

Moreover, according to an embodiment of the present invention, the image processor 200 may perform a scan conversion that enlarges or reduces an image of a certain region at a certain magnification, on the basis of the ultrasonic data corresponding to the certain region of the ultrasonic image.

In this case, the image processor 200 may perform the scan conversion such that a resolution of the scan-converted image is the same as that of the ultrasonic image or has a value higher than that of the ultrasonic image. This will be described below with reference to FIG. 5.

The ultrasonic image may display a motion of a target object as a Doppler image in addition to a grayscale ultrasonic image that is generated by scanning the target object according to the A mode, the B mode, and a motion (M) mode. The Doppler image may include a blood Doppler image (also called a color Doppler image) indicating a flow of blood, a tissue Doppler image indicating a motion of a tissue, and a spectral Doppler image that displays a moving speed of the target object as a waveform.

A B mode processor 212 extracts a B mode component from the ultrasonic data to process the B mode component. An image generation unit 220 may generate an ultrasonic image that displays a signal intensity as a brightness, on the basis of the B mode component extracted by the B mode processor 212.

Similarly, a Doppler processor 214 may extract a Doppler component from the ultrasonic data, and the image generation unit 220 may generate a Doppler image that displays a motion of a target object as a color or a waveform, on the basis of the extracted Doppler component.

The image generation unit 220 according to an embodiment may perform a volume rendering operation on volume data to generate a 3D ultrasonic image, and may also generate an elastic image that displays a degree of modification (based on a pressure) of a target object 10 as an image. Furthermore, the image generation unit 220 may express various pieces of additional information on the ultrasonic image as texts and graphics. The generated ultrasonic image may be stored in a memory 400.

The image processor 200 may further include an edge detection unit 250.

The edge detection unit 250 may analyze the ultrasonic data composing the ultrasonic image to detect an edge. In this case, an edge detection method may use a Sobel edge detection technique, a Prewitt edge detection technique, a Roberts edge detection technique, a Laplacian edge detection technique, a compass edge detection technique, or a Canny edge detection technique, but is not limited thereto.

The edge detection unit 250 may be configured with an edge detection filter based on each of the edge detection techniques, and the edge detection filter may include a mask based on each of the edge detection techniques.

Moreover, as described above, the image generation unit 220 may generate an edge detection image indicating an edge detected by the edge detection unit 250.

A display unit 230 displays the ultrasonic image generated by the image generation unit 220. The display unit 230 may display various pieces of information processed by the ultrasonic diagnostic apparatus 1000, in addition to the ultrasonic image, on a screen through a graphics user interface (GUI).

The ultrasonic diagnostic apparatus 1000 may include two or more display units 230 depending on an implementation type.

The display unit 230 include at least one of a liquid crystal display (LCD), a thin film transistor-liquid crystal display (TFT-LCD), an organic light-emitting diode (OLED), a flexible display, a 3D display, and an electrophoretic display.

Moreover, when the display unit 230 and the user input unit 500 are implemented as a touch screen by forming a layer structure, the display unit 230 may be used as an input unit that enables information to be input by a user's touch, in addition to an output unit.

The touch screen may be configured to detect a touch pressure in addition to a touch input position and a touched area. Also, the touch screen may be configured to detect a proximity touch as well as a real touch.

Herein, the term "real touch" denotes a case in which a pointer really touches a screen, and the term "proximity touch" denotes a case in which the pointer does not actually touch the screen but approaches a position which is separated from the screen by a certain distance. The pointer used herein denotes a touch instrument for really touching or proximity-touching a specific portion of a displayed screen. Examples of the pointer include an electronic pen, a finger, etc.

Although not shown, the ultrasonic diagnostic apparatus 1000 may include various sensors inside or near the touch screen, for detecting a real touch or a proximity touch on the touch screen. An example of a sensor for sensing a touch of the touch screen is a tactile sensor.

The tactile sensor denotes a sensor that senses a touch by a specific object by a degree, in which a user feels, or more. The tactile sensor may sense various pieces of information such as a roughness of a touched surface, a stiffness of a touched object, a temperature of a touched point, etc.

Moreover, an example of a sensor for sensing a touch of the touch screen is a proximity sensor. The proximity sensor denotes a sensor that detects an object approaching a detection surface or an object near the detection surface by using an electromagnetic force or infrared light without any mechanical contact.

Examples of the proximity sensor include a transmissive photosensor, a directly reflective photosensor, a mirror reflective photosensor, a high frequency oscillation-type proximity sensor, a capacitive proximity sensor, a magnetic proximity sensor, and an infrared proximity sensor.

The communicator 300 is connected to a network 30 in a wired or wireless manner to communicate with an external device or server. The communicator 300 may exchange data with a hospital server or a medical apparatus of a hospital which is connected thereto through a medical image information system (PACS). Also, the communicator 300 may perform data communication according to the digital imaging and communications in medicine (DICOM) standard.

The communicator 300 may transmit and receive data, such as an ultrasonic image, ultrasonic data, Doppler data, etc. of a target object, associated with a diagnosis of the target object over the network 30, and may also transmit and receive a medical image captured by a medical apparatus such as a computed tomography (CT) apparatus, a magnetic resonance imaging (MRI) apparatus, or an X-ray apparatus. Furthermore, the communicator 300 may receive information on a diagnosis history or treatment schedule of a patient from a server, and use a diagnosis of a target object. In addition, the communicator 300 may perform data communication with a portable terminal of a doctor or a patient, in addition to a server or medical apparatus of a hospital.

The communicator 300 may be connected to the network 30 in a wired or wireless manner, and may exchange data with a server 32, a medical apparatus 34, or a portable terminal 36. The communicator 300 may include one or more elements that enable communication with an external device, and may, for example, include a short-distance communication module 310, a wired communication module 320, and a mobile communication module 330.

The short-distance communication module 310 denotes a module for short-distance communication within a certain distance. In short-distance communication technology according to an embodiment of the present invention, there may be wireless LAN, Wi-Fi, Bluetooth, Zigbee, Wi-Fi direct (WFD), ultra wideband (UWB), infrared data association (IrDA), Bluetooth low energy (BLE), and near field communication (NFC), but the short-distance communication technology is not limited thereto.

The wired communication module 320 denotes a module for communication using an electrical signal or an optical signal. Wired communication technology according to an embodiment may include a pair cable, a coaxial cable, an optical fiber cable, an Ethernet cable.

The mobile communication module 330 transmits and receives a radio frequency (RF) signal to and from a base station, an external terminal, and a server over a mobile communication network. Here, the RF signal may include various types of data based on transmission and reception of a voice call signal, a video call signal, or a letter/multimedia message.

The memory 400 stores various pieces of information processed by the ultrasonic diagnostic apparatus 1000. For example, the memory 400 may store medical data, such as input/output ultrasonic data and ultrasonic images, associated with a diagnosis of a target object, and may also store an algorithm or a program which is executed in the ultrasonic diagnostic apparatus 1000.

The memory 400 may be configured with various kinds of storage mediums such as a flash memory, a hard disk, an EEPROM, etc. Also, the ultrasonic diagnostic apparatus 1000 may operate a web storage or a cloud server which performs a storage function of the memory 400 on a web.

The user input unit 500 generates input data which is input by a user for controlling an operation of the ultrasonic diagnostic apparatus 1000. The user input unit 500 may include hardware elements such as a keypad, a mouse, a touch pad, a trackball, a jog switch, but is not limited thereto. As another example, the user input unit 500 may further include various sensors such as an electrocardiogram (ECG) measurement module, a breath measurement sensor, a voice recognition sensor, a gesture recognition sensor, a fingerprint recognition sensor, an iris recognition sensor, a depth sensor, a distance sensor, etc.

In particular, the user input unit 500 may further include the touch screen in which the touch pad and the display unit 230 form the layer structure.

In this case, the ultrasonic diagnostic apparatus 1000 may display a specific mode ultrasonic image and a control panel for an ultrasonic image, on the touch screen. In addition, the ultrasonic diagnostic apparatus 1000 may sense a user's touch gesture for an ultrasonic image through the touch screen.

Examples of a user's touch gesture described herein may include a tap, a touch and hold, a double tap, a drag, panning, a flick, a drag and drop, a swipe, and a pinch.

The term "tap" denotes a motion in which a user touches a screen with a finger or an electronic pen, and immediately raises the finger or the electronic pen without moving.

The term "touch and hold" denotes a motion in which a user touches a screen with a finger or an electronic pen, and maintains the touch for a threshold period of time (for example, two seconds) or longer. That is, the "touch and hold" denotes a case in which a time difference between a touch-in time and a touch-out time is equal to or longer than the threshold period of time (for example, two seconds). When the touch input is maintained for the threshold period of time or longer in order for the user to determine whether the user input is the tap or the touch and hold, a feedback signal may be provided visually, acoustically, or tactually. The threshold time may be changed depending an implementation example.

The term "double tap" denotes a motion in which a user touches a screen twice with a finger or an electronic pen.

The term "drag" denotes a motion in which a user touches a screen with a finger or an electronic pen, and, with the user maintaining the touch, the user moves the finger or the electronic pen to a different position of the screen. Due to the drag motion, an object is moved, or a panning motion to be described below is performed.

The "panning" denotes a case in which a user performs the drag motion without selecting an object. In the panning, since a specific object is not selected, an object does not move in a page, and the page itself moves in a screen, or a group of objects moves in the page.

The term "flick" denotes a motion in which a user performs a drag motion with a finger or an electronic pen at a threshold speed (for example, 100 pixels/s) or more. The drag (or the panning) and the flick may be determined according to whether a moving speed of the finger or electronic pen is equal to or higher than the threshold speed (for example, 100 pixels/s).

The term "drag and drop" denotes a motion in which a user drags an object to a certain position of a screen with a finger or an electronic pen.

The term "pinch" denotes a motion in which a user touches a screen with two fingers and moves the two fingers in a different direction. The pinch is a gesture for enlarging (pinch open) or reducing (pinch close) an object or a page, and an enlargement value or a reduction value is determined according to a distance between the two fingers.

The term "swipe" denotes a motion in which a user touches an object on a screen with a finger or an electronic pen, and moves the object by a certain distance in a horizontal or vertical direction. A motion in a diagonal direction may not be recognized as a swipe event.

The ultrasonic diagnostic apparatus 1000 according to an embodiment of the present invention may physically include some buttons, frequently used by a user, from among a plurality of buttons included in a control panel of general ultrasonic diagnostic apparatuses, and the other buttons may be provided through a type of GUI on the touch screen.

The controller 600 controls an overall operation of the ultrasonic diagnostic apparatus 1000. That is, the controller 600 may control operations between the probe 20, the ultrasonic transceiver 100, the image processor 200, the communicator 300, the memory 400, and the user input unit 500 which are illustrated in FIG. 1.

Some or all of the probe 20, the ultrasonic transceiver 100, the image processor 200, the communicator 300, the memory 400, the user input unit 500, and the controller 600 may be operated by a software module, but are not limited thereto. Some of the above-described elements may be operated by a hardware module. Also, at least some of the ultrasonic transceiver 100, the image processor 200, and the communicator 300 may be included in the controller 600, but are not limited to the implementation type.

The block diagram of the ultrasonic diagnostic apparatus 1000 of FIG. 1 is a block diagram according to an embodiment of the present invention. The elements of the block diagram may be integrated, added, or omitted depending on a specification of an actually implemented cache memory system. That is, depending on the case, two or more elements may be integrated into one element, or one element may be subdivided into two or more elements. Also, a function performed by each element is for describing an embodiment of the present invention, and each element or a detailed operation thereof does not limit the scope and spirit of the present invention.

Figure 2:
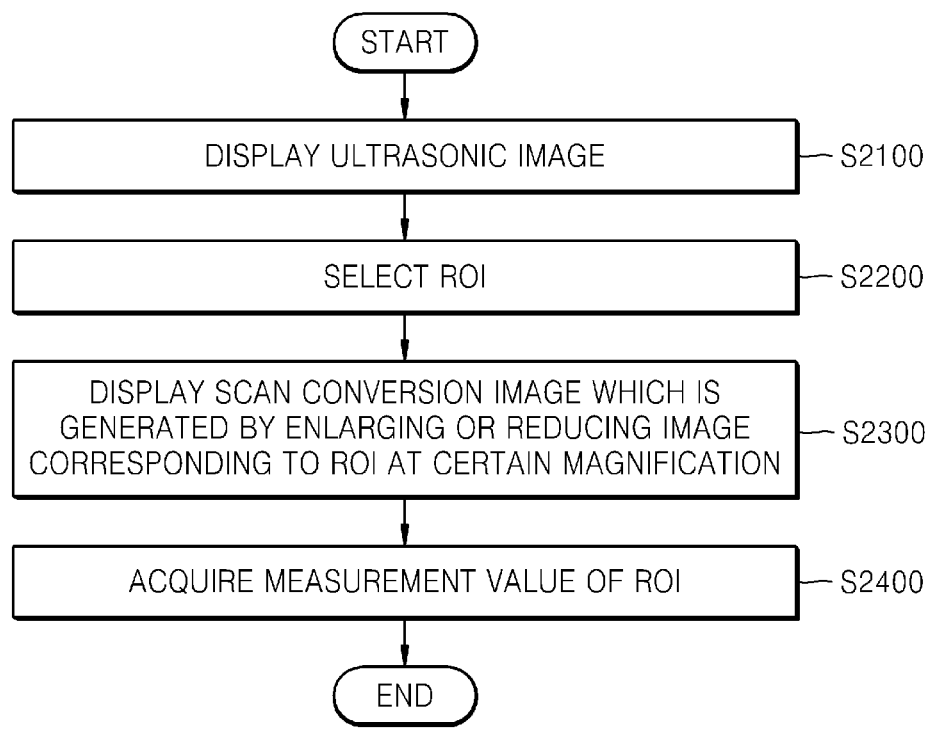
FIG. 2 is a flowchart illustrating a method of operating an ultrasonic diagnostic apparatus according to an embodiment of the present invention.

FIG. 2 is a flowchart illustrating a method of operating the ultrasonic diagnostic apparatus according to an embodiment of the present invention.

Figure 3:
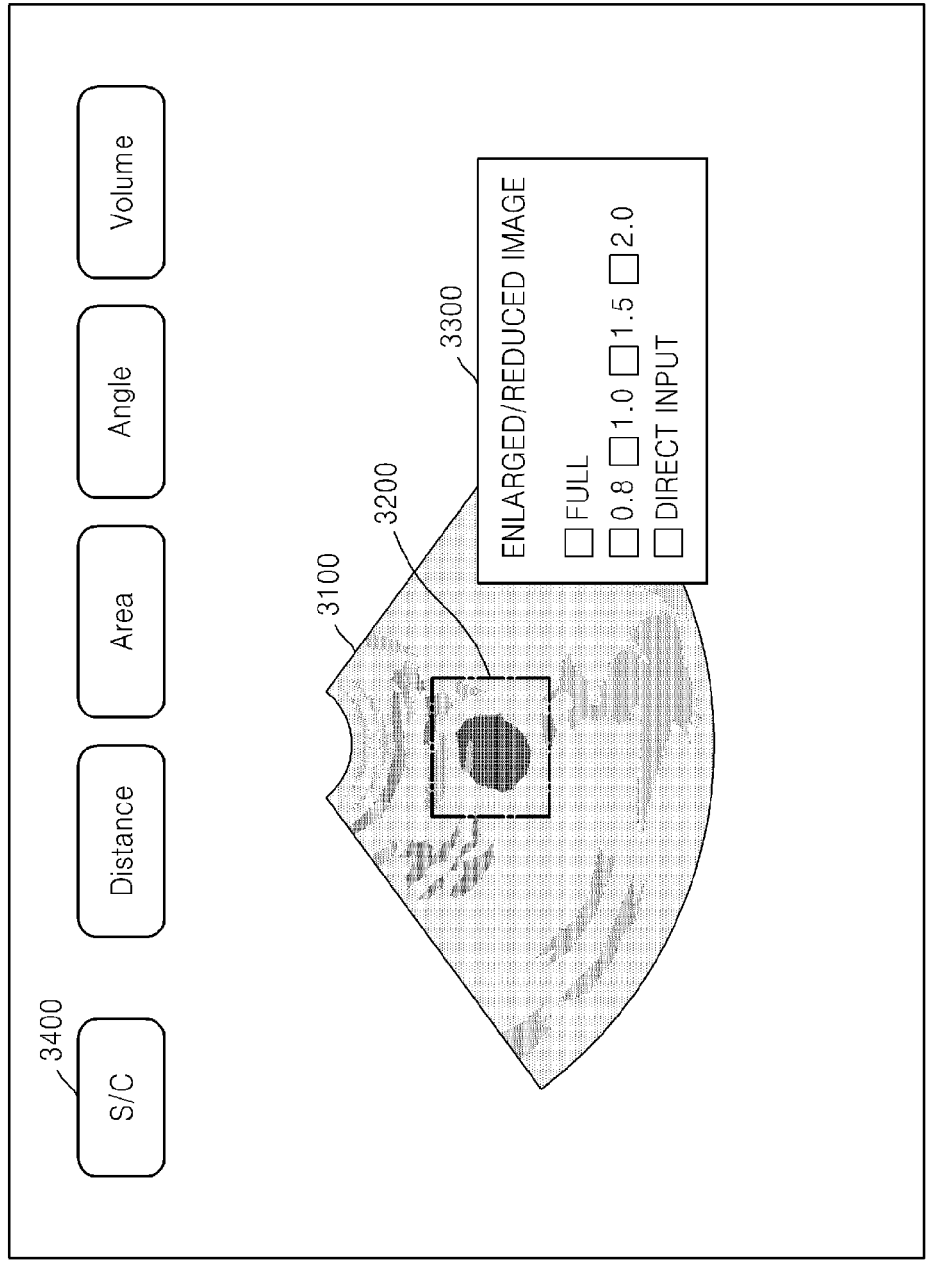
FIGS. 3 to 8 are diagrams for explaining the method of operating the ultrasonic diagnostic apparatus according to the embodiment of FIG. 2.

Referring to FIG. 2, the ultrasonic diagnostic apparatus 1000 displays an ultrasonic image 3100 (see FIG. 3), which is generated on the basis of acquired ultrasonic data, in the display unit 230 in operation S2100. Here, the ultrasonic image 3100, as illustrated in FIG. 3, may be the B mode ultrasonic image, but is not limited thereto.

The ultrasonic diagnostic apparatus 1000 may select a region of interest (ROI) 3200 in the ultrasonic image 3100 in operation S2200.

According to an embodiment of the present invention, the ultrasonic diagnostic apparatus 1000 may automatically select the ROI, or may select the ROI on the basis of a user input.

Here, the user input may be an input using an input unit such as a mouse or a keypad, and when the display unit 230 is configured with the touch screen, the touch input may be a touch input using a touch instrument (for example, a finger, an electronic pen, or the like).

The user input may be an input for selecting a certain region in an ultrasonic image. Alternatively, the user input may be an input for selecting a specific object in the ultrasonic image, in which case a certain region including the selected specific object may be selected as an ROI 3200 (see FIG. 3).

Alternatively, the user input may be an input of a coordinate value of a certain region in the ultrasonic image.

As illustrated in FIG. 3, the selected ROI 3200 may be displayed by the display unit 230.

Referring again to FIG. 2, the ultrasonic diagnostic apparatus 1000 may perform a scan conversion that enlarges or reduces an image corresponding to the selected ROI at a certain magnification, and display the scan-converted image in operation S2300.

Here, the certain magnification may be a magnification predetermined by the ultrasonic diagnostic apparatus 1000 or an external server, or may be a magnification that is input by a user.

For example, as illustrated in FIG. 3, when the ROI 3200 is selected, the ultrasonic diagnostic apparatus 1000 may display a menu window 3300. At this time, the ultrasonic diagnostic apparatus 1000 may receive a selection or an input at a certain magnification through the menu window 3300. Also, a plurality of certain magnifications may be selected or input.

In FIG. 3, the menu window 3300 is illustrated as being displayed as a popup window, but is not limited thereto. The menu window 3300 may be displayed by a separate display unit (not shown).

The image processor 200 may perform a scan conversion such that the image corresponding to the ROI is enlarged or reduced at a certain magnification.

For example, when an ROI and a certain magnification are selected and an input for selecting a scan conversion button 3400 is received, the image processor 200 may perform a scan conversion such that an image corresponding to the selected ROI is enlarged or reduced at the selected magnification.

At this time, the image processor 200 may perform the scan conversion such that a resolution of the scan-converted image is the same as that of the ultrasonic image or has a value higher than that of the ultrasonic image.

Figure 4:
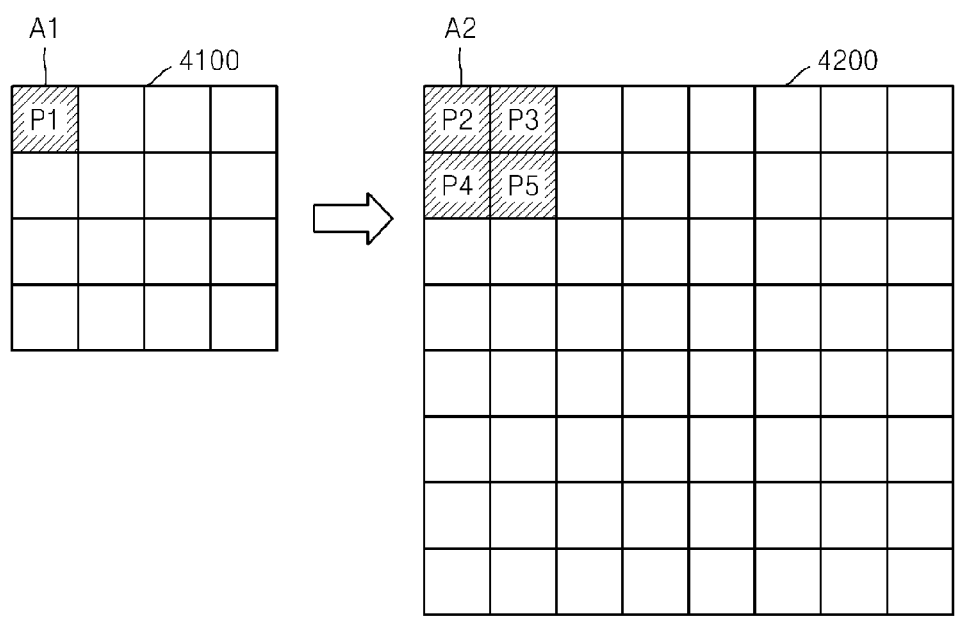

For example, referring to FIG. 4, an image 4100 corresponding to an ROI in an ultrasonic image may be composed of sixteen (=4*4) pixel values (in the drawing, one tetragonal shape indicates one pixel). In this case, when performing a scan conversion that enlarges the image 4100 corresponding to the ROI by two times, a first region A1 of the image 4100 corresponding to the ROI may correspond to a second region A2 of an enlarged image 4200, in the ultrasonic image.

Therefore, a first region A1, is composed of one pixel (in the drawing, one tetragonal shape), and a second region A2 is composed of four (=2*2) pixel values (in the drawing, four tetragonal shapes).

Therefore, the first region A1, includes a first pixel value P1, and the second region A2 includes second to fifth pixel values P2 to P5.

In this case, the image processor 200 does not set the second to fifth pixel values P2 to P5 to the same value as the first pixel value P1, and may set the second to fifth pixel values P2 to P5 to different pixel values.

Accordingly, a resolution of the enlarged image 4200 may have the same value as a resolution of the image 4100 corresponding to the ROI in the ultrasonic image.

When an ultrasonic image is enlarged by n times, the ultrasonic diagnostic apparatus 1000 according to an embodiment of the present invention performs a scan conversion for generating an enlarged image having $n^2$ times the pixel values, thus maintaining a resolution of the enlarged image.

Alternatively, the ultrasonic diagnostic apparatus 1000 may further increase the number of pixel values composing an enlarged image to perform a scan conversion, thus enabling the resolution of the enlarged image to have a value higher than a resolution of an image corresponding to an ROI in an ultrasonic image.

The scan conversion method has been described above as merely an example, and is not limited thereto. The ultrasonic diagnostic apparatus 1000 may perform a scan conversion by using various methods.

The ultrasonic diagnostic apparatus 1000 displays a scan conversion image and a certain magnification in the display unit 230.

At this time, when a plurality of certain magnifications are selected, the ultrasonic diagnostic apparatus 1000 may perform a scan conversion that enlarges or reduces an image corresponding to an ROI at the selected magnifications, and display the scan-converted image in the display unit 230.

Figure 5:
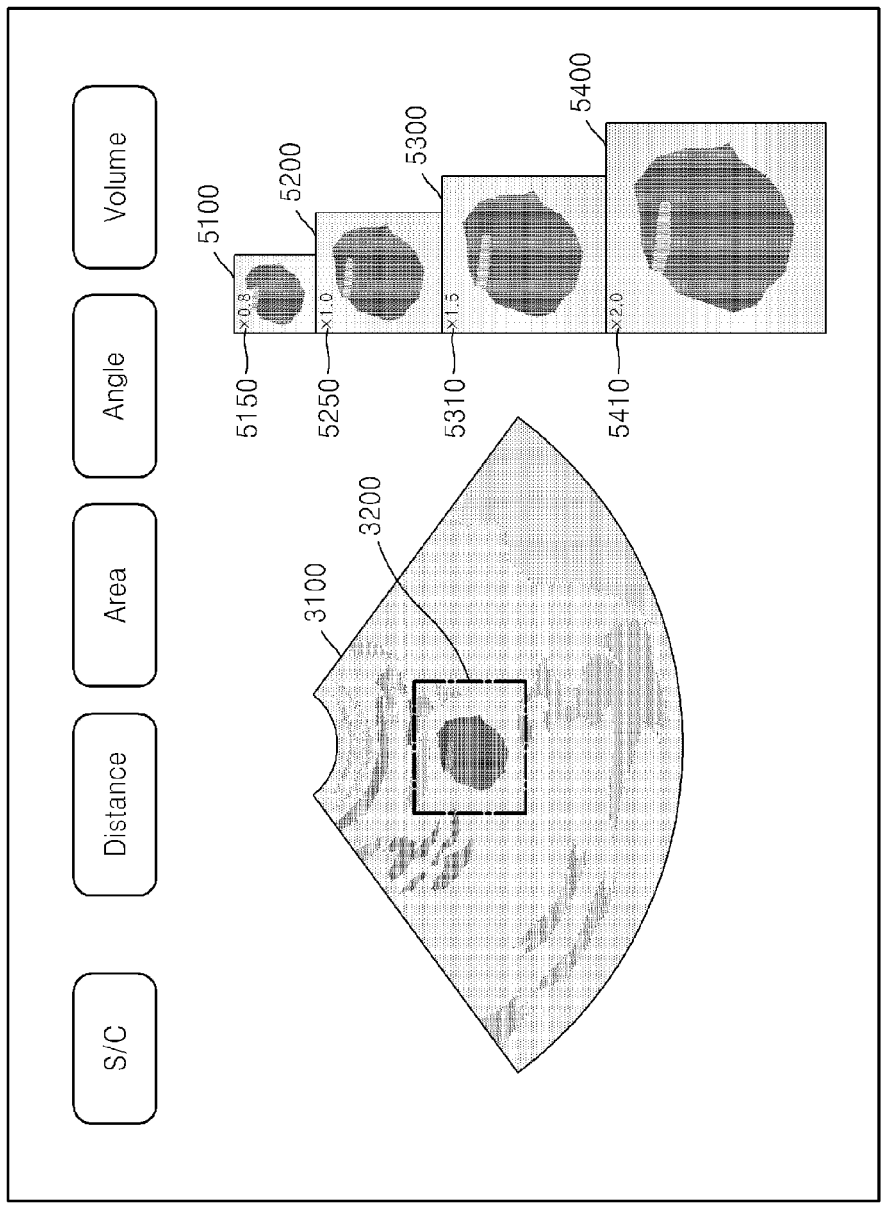

For example, as illustrated in FIG. 5, when first to fourth magnifications are selected, the ultrasonic diagnostic apparatus 1000 may sequentially display a first scan conversion image 5100 scan-converted at the first magnification, a second scan conversion image 5200 scan-converted at the second magnification, a third scan conversion image 5300 scan-converted at the third magnification, and a fourth scan conversion image 5400 scan-converted at the first magnification in the display unit 230.

In FIG. 5, it is illustrated that the ultrasonic diagnostic apparatus 1000 displays a plurality of the scan conversion images 5100, 5200, 5300 and 5400 in a lengthwise direction at a right side of the ultrasonic image, but the present invention is not limited thereto. The ultrasonic diagnostic apparatus 1000 may display the plurality of scan conversion images 5100, 5200, 5300 and 5400 in various regions such as an upper side, left side, and lower side of the ultrasonic image.

Moreover, the ultrasonic diagnostic apparatus 1000 may display the plurality of scan conversion images 5100, 5200, 5300 and 5400 and magnifications 5150, 5250, 5350 and 5450 in a one-to-one correspondence relationship. At this time, the ultrasonic diagnostic apparatus 1000 may display a magnification in one region of a scan conversion image.

The ultrasonic diagnostic apparatus 1000 may acquire a measurement value of an ROI on the basis of the scan conversion images in operation S2400.

At this time, the most suitable image for measuring an object of interest (OOI) can be selected from among the plurality of images scan-converted at the respective magnifications.

The ultrasonic diagnostic apparatus 1000 may acquire a measurement value of the OOI on the basis of the selected scan conversion image.

In measuring the OOI, an image reduced to a certain magnification may be more suitable, or an image enlarged to a certain magnification may be more suitable, depending on a kind of OOI and a kind of numerical value to be measured.

Figure 6:
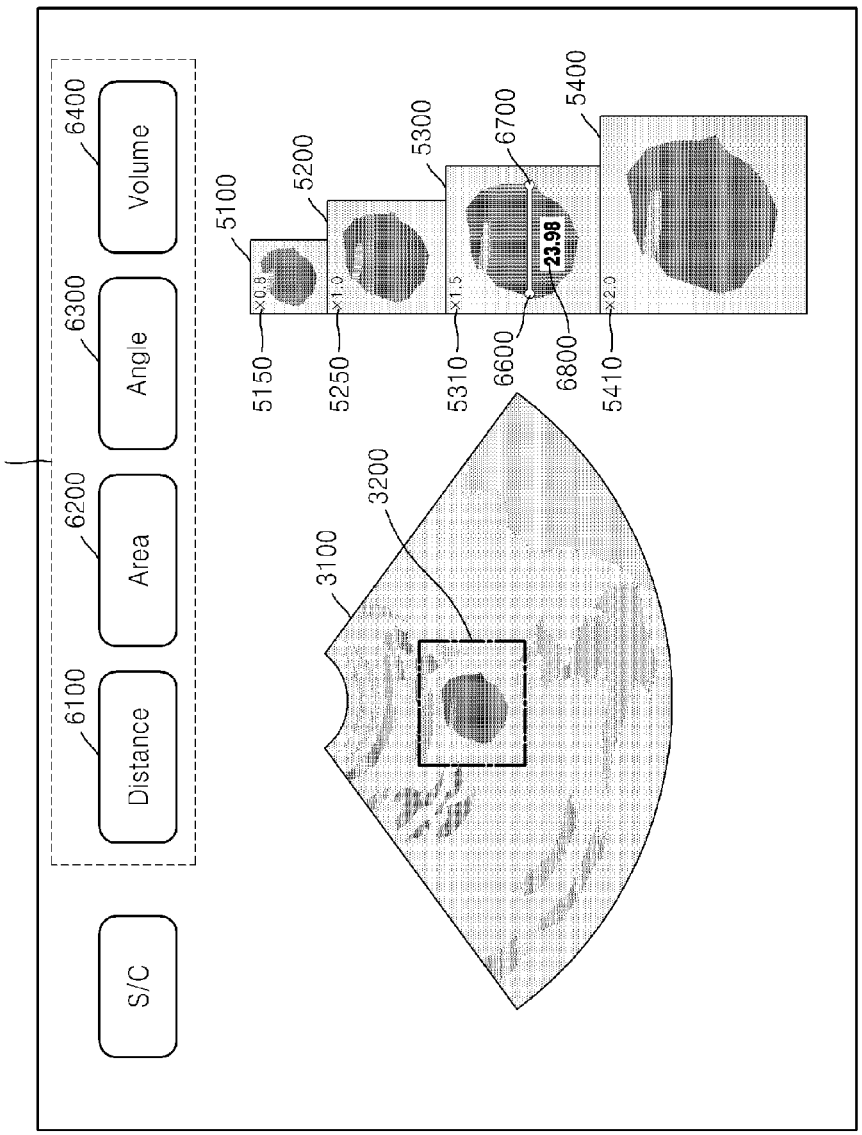
Figure 7:
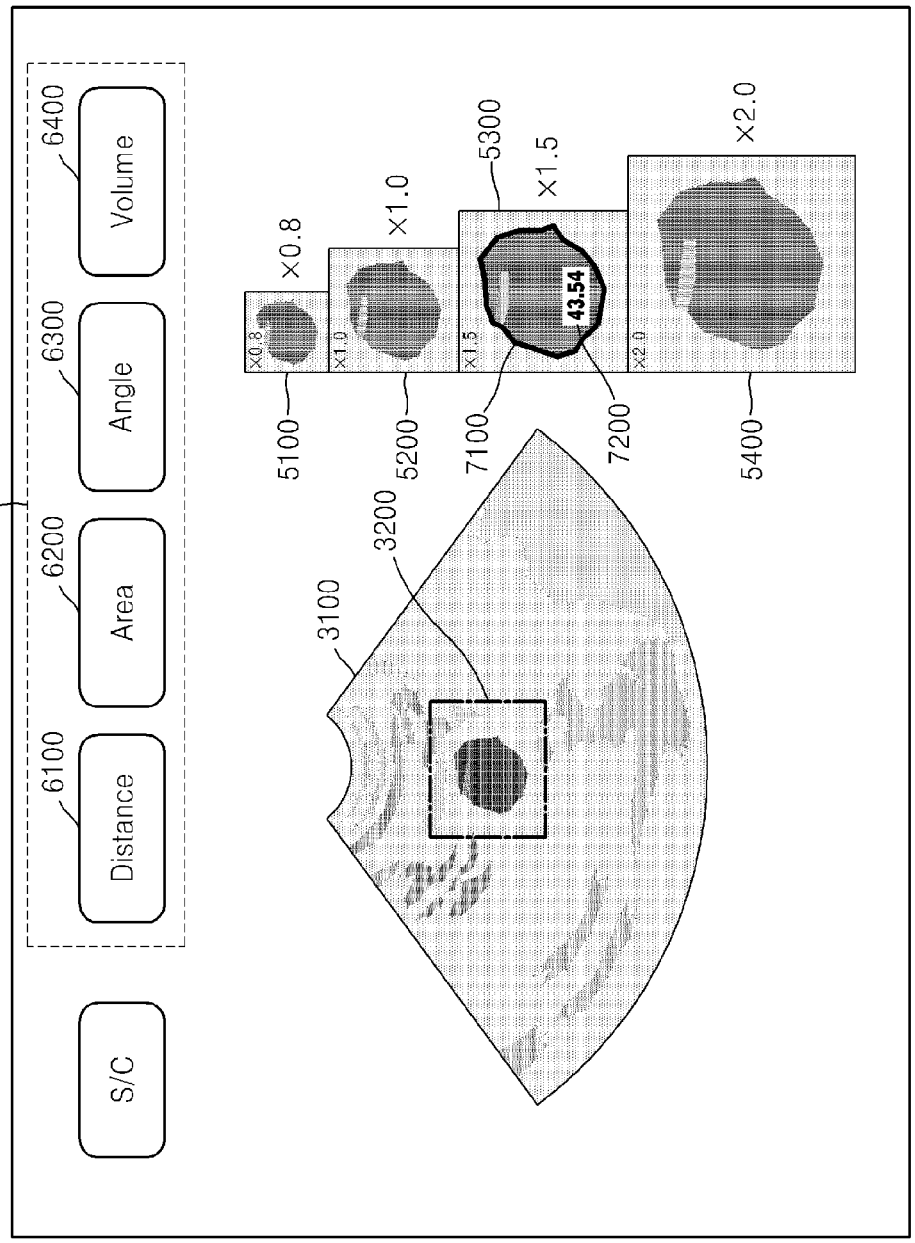

As illustrated in FIGS. 6 and 7, when a user selects the most suitable third scan conversion image 5300 from among several enlarged/reduced scan conversion images (the first to fourth scan conversion images), the ultrasonic diagnostic apparatus 1000 may acquire a measurement value of an OOI on the basis of the third scan conversion image 5300.

Alternatively, the ultrasonic diagnostic apparatus 1000 may automatically select a scan conversion image on the basis of a kind of OOI and a kind of numerical value to be measured, and may measure a numerical value of the OOI on the basis of the selected scan conversion image.

Therefore, the ultrasonic diagnostic apparatus 1000 can select the most suitable scan conversion image, and may accurately measure an OOI.

Measurement values of an ROI may include at least one of a distance, an area, an angle, and a volume of an OOI included in the ROI, but is not limited thereto. For another example, the measurement values of the ROI may include various numerical values, such as a circumference of the ROI, necessary for a diagnosis.

For example, as illustrated in FIGS. 6 and 7, the ultrasonic diagnostic apparatus 1000 may display a measurement menu window 6500 including at least one of a distance measurement button 6100, an area measurement button 6200, an angle measurement button 6300, and a volume measurement button 6400.

As illustrated in FIG. 6, when the user selects the distance measurement button 6100, a first point 6600 and a second point 6700 may be selected by an input unit such as a mouse or a touch instrument. Alternatively, coordinate values of the first and second points 6600 and 6700 may be input.

At this time, the ultrasonic diagnostic apparatus 1000 may measure a distance between the first and second points 6600 and 6700, and display the measured distance 6800 in the scan conversion image 5300.

As illustrated in FIG. 7, when the user selects the area measurement button 6200, a specific region 7100 of a scan conversion image may be selected by the input unit such as the mouse or the touch instrument. Alternatively, the ultrasonic diagnostic apparatus 1000 may automatically select the specific region 7100 on the basis of a shape of an OOI.

At this time, the ultrasonic diagnostic apparatus 1000 may measure an area of the selected region, and display the measured area 7200 in the scan conversion image 5300.

Figure 8:
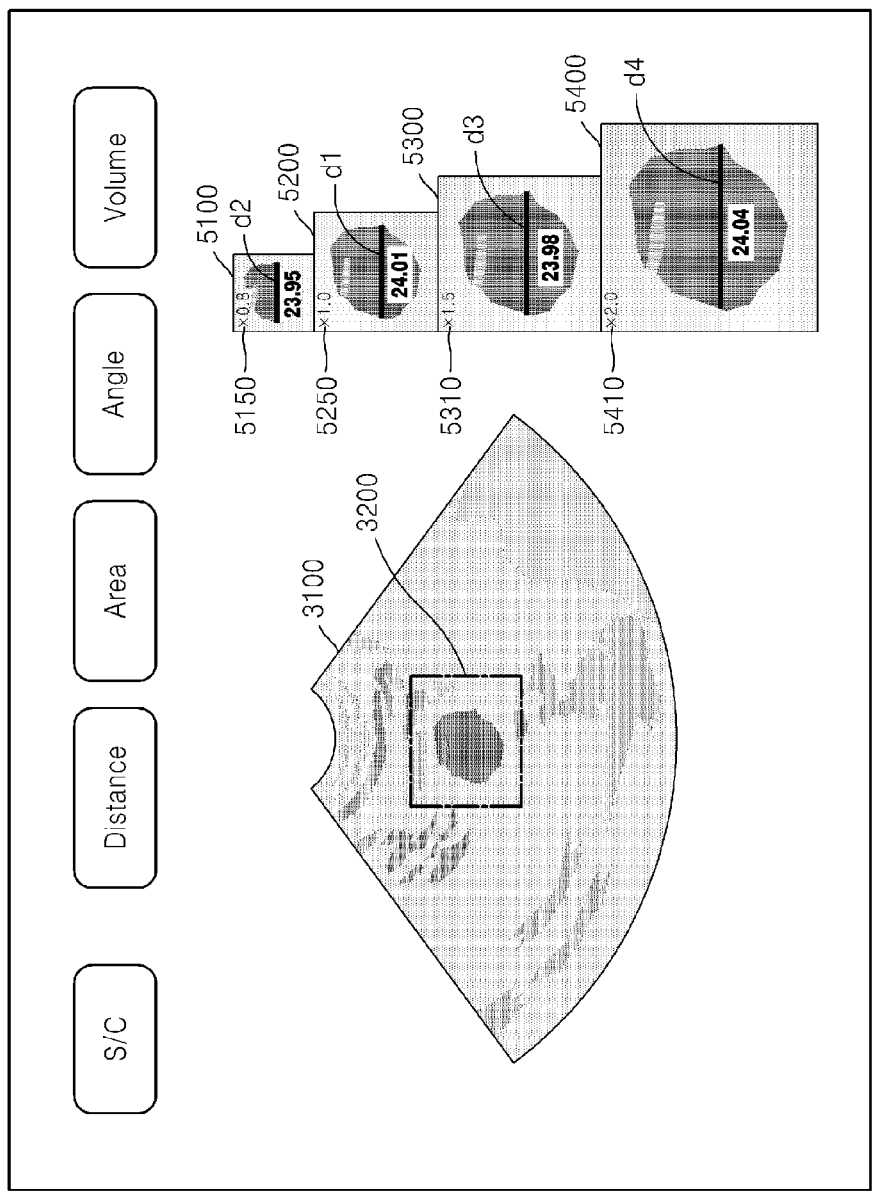

As illustrated in FIG. 8, the ultrasonic diagnostic apparatus 1000 may acquire a measurement value of an OOI from each of the plurality of images 5100, 5200, 5300 and 5400 scan-converted according to the respective magnifications.

For example, when the user selects first and second points from the second scan conversion image 5200, the ultrasonic diagnostic apparatus 1000 may measure and display a first distance d1 between the first and second points.

Moreover, the ultrasonic diagnostic apparatus 1000 may measure second to fourth distances d2 to d4, corresponding to the first distance d1, from the respective first, third, and fourth scan conversion images 5100, 5300 and 5400, and display the measured distance values.

When a plurality of measurement values are respectively acquired from a plurality of scan conversion images, the ultrasonic diagnostic apparatus 1000 may further display a value which is calculated on the basis of the acquired plurality of measurement values.

For example, the ultrasonic diagnostic apparatus 1000 may display variously calculated values such as an average value, variance, and standard deviation of a first measurement value measured from the first scan conversion image 5100, a second measurement value measured from the second scan conversion image 5200, a third value measured from the third scan conversion image 5300, and a fourth measurement value measured from the fourth scan conversion image 5400.

Therefore, the user compares the values measured and the values calculated from the respective scan conversion images, thus acquiring an accurate measurement value of an OOI.

Figure 9:
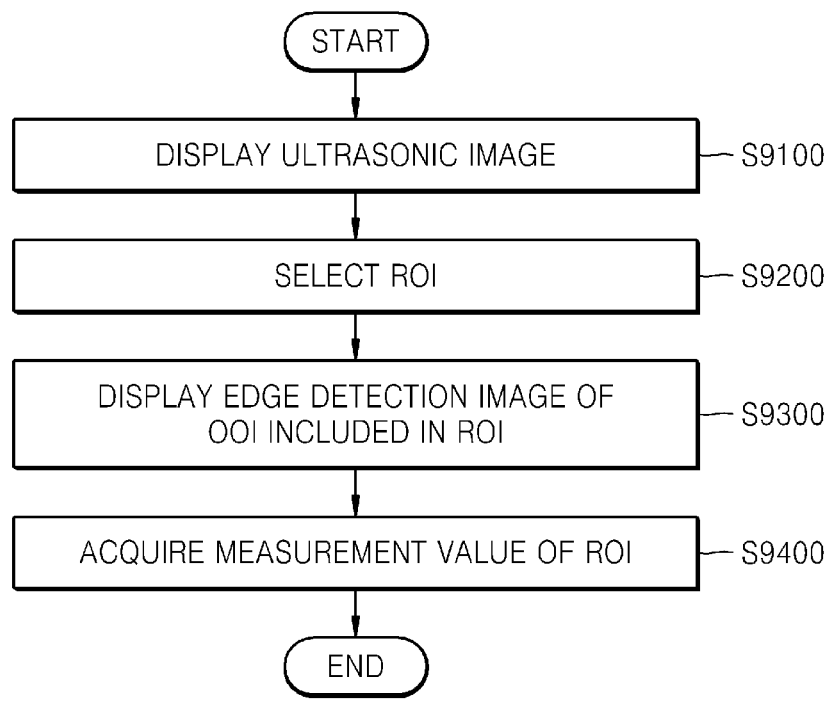
FIG. 9 is a flowchart illustrating a method of operating an ultrasonic diagnostic apparatus according to another embodiment of the present invention.

FIG. 9 is a flowchart illustrating a method of operating the ultrasonic diagnostic apparatus according to another embodiment of the present invention.

Referring to FIG. 9, the ultrasonic diagnostic apparatus 1000 displays an ultrasonic image, which is generated on the basis of acquired ultrasonic data, in the display unit 230 in operation S9100. Operation S9100 corresponds to operation S2100 of FIG. 2, and thus, a detailed description thereof will not be provided here.

The ultrasonic diagnostic apparatus 1000 may select the ROI 3200 in the ultrasonic image 3100 in operation S9200.

According to an embodiment of the present invention, the ultrasonic diagnostic apparatus 1000 may automatically select the ROI, or may select the ROI on the basis of a user input.

Operation S9200 corresponds to operation S2200 of FIG. 2, and thus, a detailed description thereof will not be provided here.

The ultrasonic diagnostic apparatus 1000 may detect an edge of the OOI included in the ROI on the basis of image data corresponding to the selected ROI, and display an edge detection image indicating the detected edge in operation S9300.

Figure 10:
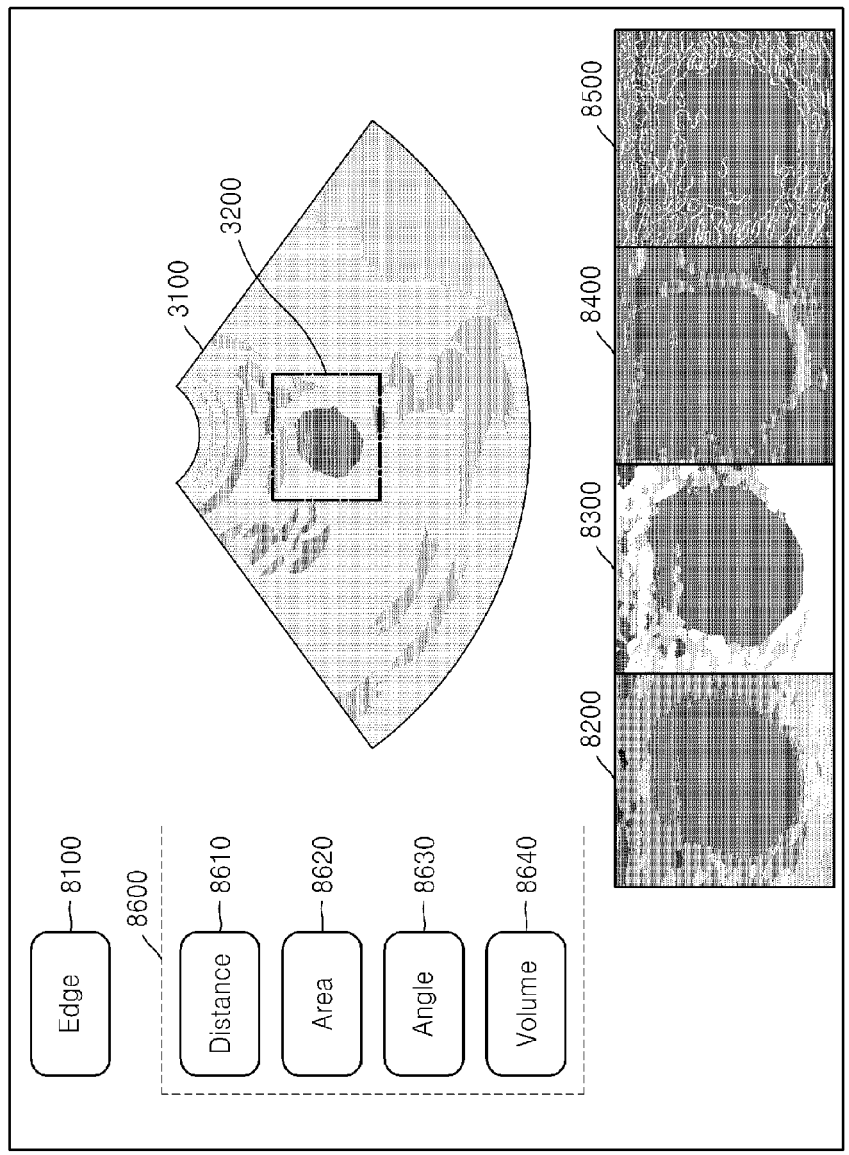
FIGS. 10 and 11 are diagrams for explaining the method of operating the ultrasonic diagnostic apparatus according to the other embodiment of FIG. 9.

For example, as illustrated in FIG. 10, when a user input for selecting an edge detection button 8100 is received, the ultrasonic diagnostic apparatus 1000 may detect the edge of the OOI included in the selected ROI.

The edge of the ROI may be a portion in which a color or a brightness shown in an image in the ROI is rapidly changed. For example, the edge may be a portion in which a brightness of an image is changed from a low value to a high value or from the high value to the low value.

Therefore, the edge may be located at a discontinuous point of pixel values composing an image or a discontinuous value of pixel differentiation values.

The ultrasonic diagnostic apparatus 1000 may detect an edge of an OOI included in an ROI by using the edge features. The edge of the OOI notifies information on a position, shape, and size of the OOI.

The edge detection unit 250 analyzes image data corresponding to the ROI to detect the edge of the OOI included in the ROI. In this case, the edge detection unit 250 may detect the edge by using the Sobel edge detection technique, the Prewitt edge detection technique, the Roberts edge detection technique, the Laplacian edge detection technique, the compass edge detection technique, or the Canny edge detection technique as an edge detection method.

However, the edge detection unit 250 does not restrictedly use the above-described detection techniques, and in addition, may use a generally known edge detection technique.

The edge detection unit 250 may be configured with an edge filter based on the techniques, and may include a mask.

For example, a Sobel edge filter detects an edge on the basis of a value which is obtained by differentiating image data on each of an x-axis and a y-axis one time by using a primary differential operator.

A mask of the Sobel edge filter may extract edges in all directions, and average a plurality of protruding pixel values. Accordingly, the Sobel edge filter is robust to noise, and more sensitively reacts to a diagonal-direction edge than a vertical-direction edge and a horizontal-direction edge.

A Prewitt edge filter shows an almost same result value as that of the Sobel edge filter, and has a shorter response time than the Sobel edge filter. Also, a mask of the Prewitt edge filter places lower weight on a brightness change than the mask of the Sobel edge filter, and thus, in extracting an edge, the Prewitt edge filter allows the edge to have low weight.

A Roberts edge filter is a very sensitive filter, and has a fast calculation speed. Also, a mask of the Roberts edge filter has a smaller size than the masks of the other edge filters, and thus, the Roberts edge filter is vulnerable to noise because it is unable to average a plurality of protruding pixel values.

A compass edge filter extracts an edge by using the maximum slope value of eight slopes.

A Laplacian edge filter uses a secondary differential operator, and has a fast calculation speed. Also, a mask of the Laplacian edge filter may extract edges in all directions. The Laplacian edge filter removes values corresponding to a low frequency component, and allows high frequency components to be more clearly shown, thus detecting a sharp edge compared to the other edge filters.

A Canny edge filter finds a point, in which a darkness and brightness change is greater than the other points, in an input image, and detects an edge in a scheme that traces the found point and extracts a plurality of points of a line formed by the trace. The Canny edge filter is a filter which satisfies a detectability (an ability to detect all real edges), a locality (minimizing a difference between a real edge and a detected edge), and a responsibility (a single response to each edge), and may be configured with a four-stage algorithm.

The ultrasonic diagnostic apparatus 1000 may display an edge detection image indicating a detected edge.

The edge detection image is an image in which the edge of the OOI detected by the edge detection unit 250 is displayed.

In this case, the edge detection image may be an image displaying an edge detected from an image which is generated by enlarging an ultrasonic image corresponding to an ROI at a certain magnification.

For example, the image processor 200 may perform a scan conversion that enlarges an ultrasonic image corresponding to an ROI at a certain magnification. The scan conversion has been described above with reference to FIGS. 2 and 3, and thus, a detailed description thereof will not be provided here.

Subsequently, the edge detection unit 250 may detect an edge on the basis of the scan conversion image data. Here, the certain magnification may be a predetermined magnification or a magnification input from a user.

The above description has been made on a case in which the ultrasonic diagnostic apparatus 1000 displays an edge detected from an image which is generated by enlarging an image of an ROI at a certain magnification, but the ultrasonic diagnostic apparatus 1000 is not limited thereto. The ultrasonic diagnostic apparatus 1000 may display an edge detected from an image which is generated by reducing the image of the ROI at a certain magnification.

The ultrasonic diagnostic apparatus 1000, as described above, may display a plurality of edge detection images 8200, 8300, 8400 and 8500. The plurality of edge detection images 8200, 8300, 8400 and 8500 may be images indicating respective edges that are detected by different edge detection methods.

For example, a first edge detection image 8200 may be an edge detection image which is generated by using the Sobel edge detection technique, and a second edge detection image 8300 may be an edge detection image which is generated by using the Canny edge detection technique.

Moreover, the other third and fourth edge detection images 8400 and 8500 may be edge detection images which are generated by different edge detection techniques.

An edge detection image may be an image which is generated by combining an edge, detected by an edge detection technique, and the original image of an ROI.

The edge detection image generated by combining the detected edge and the original image of the ROI may indicate a similarity between the edge detected by the edge detection technique and an edge of the ROI shown in the original image.

The ultrasonic diagnostic apparatus 1000 may acquire a measurement value of the ROI on the basis of the edge detection image in operation S9400.

The user may select the most suitable image for measuring an OOI from among the edge detection images based on the respective edge detection techniques.

The ultrasonic diagnostic apparatus 1000 may acquire a measurement value of the OOI on the basis of the selected image.

Measurement values of an ROI may include at least one of a distance, an area, an angle, and a volume of an OOI included in the ROI, but is not limited thereto. As another example, the measurement values of the ROI may include various numerical values, such as a circumference of the ROI, necessary for a diagnosis.

An edge detection image clearly shows an edge of an OOI included in an ROI, and thus, the ultrasonic diagnostic apparatus 1000 may accurately measure a distance, an area, an angle, and a volume of the OOI on the basis of the edge shown in the edge detection image.

Figure 11:
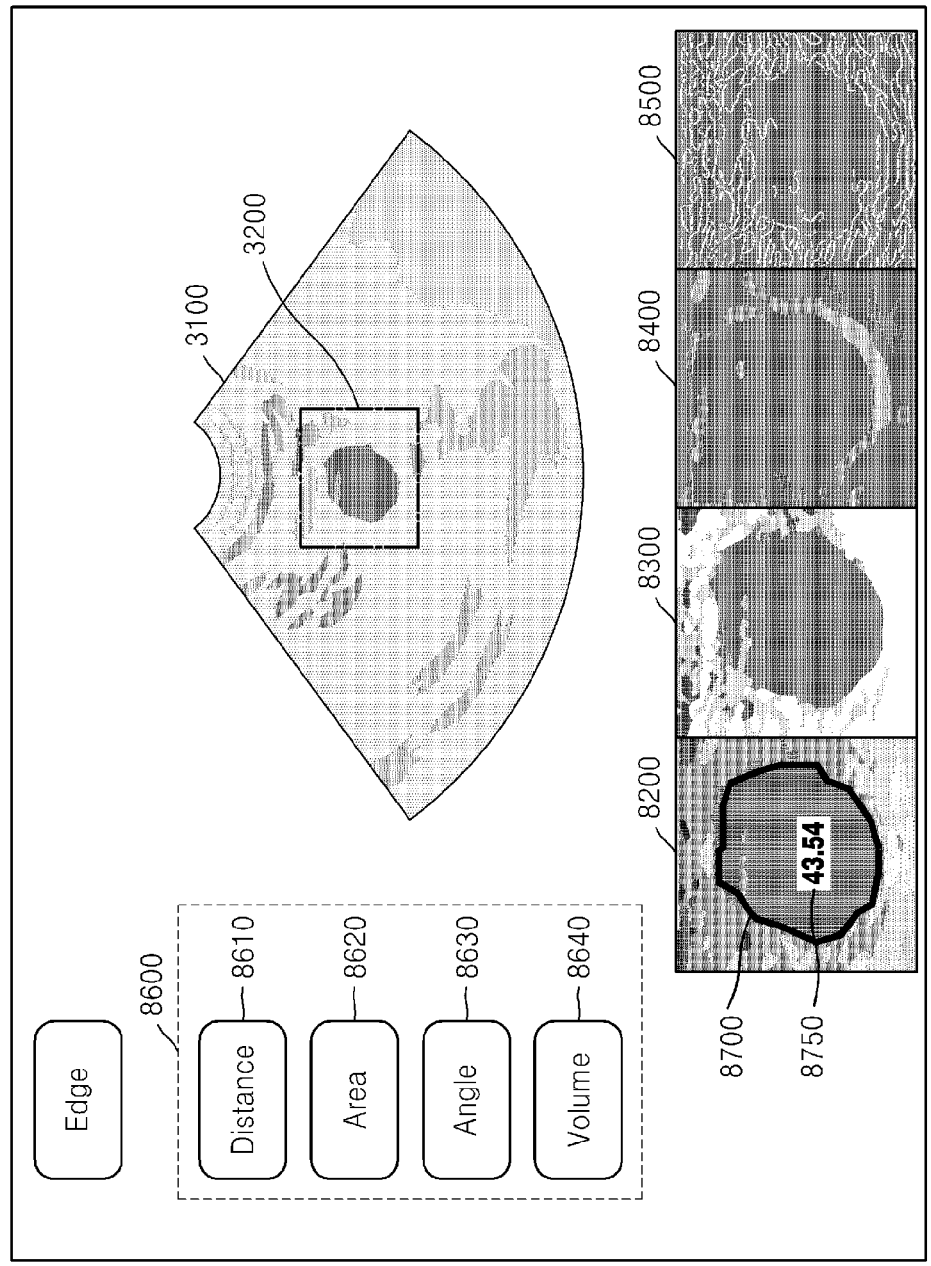

For example, as illustrated in FIGS. 10 and 11, the ultrasonic diagnostic apparatus 1000 may display a measurement menu window 8600 including at least one of a distance measurement button 8610, an area measurement button 8620, an angle measurement button 8630, and a volume measurement button 8640.

At this time, when an input for selecting the area measurement button 8620 is received, as illustrated in FIG. 11, the ultrasonic diagnostic apparatus 1000 may automatically extract a closed curve 8700 along the edge of the OOI detected from the edge detection image, and display the closed curve 8700.

Therefore, the ultrasonic diagnostic apparatus 1000 may measure an area of a region enclosed by the closed curve 8700.

In addition, the ultrasonic diagnostic apparatus 1000 can accurately measure a distance, angle, or volume of the OOI on the basis of the edge shown in the edge detection image.

Moreover, the ultrasonic diagnostic apparatus 1000 may display a measurement value 8750 in the display unit 230.

The ultrasonic diagnostic apparatus 1000 may acquire a measurement value of an OOI from each of a plurality of edge detection images. In this case, the ultrasonic diagnostic apparatus 1000 may display the acquired plurality of measure values, and may further display a value which is calculated on the basis of the acquired plurality of measurement values.

For example, the ultrasonic diagnostic apparatus 1000 may display variously calculated values such as an average value, a variance, and a standard deviation of a first measurement value measured from the first edge detection image 8200, a second measurement value measured from the second edge detection image 8300, a third value measured from the third edge detection image 8400, and a fourth measurement value measured from the fourth edge detection image 8500.

Therefore, the user may compare the values measured and the values calculated from the respective edge detection images, thus acquiring an accurate measurement value of an OOI.

The ultrasonic diagnostic apparatus and the method of operating the same according to the present invention may also be embodied as computer readable codes on a computer readable recording medium. The computer readable recording medium is any data storage device that can store data which can be thereafter read by a computer system. Examples of the computer readable recording medium include read-only memory (ROM), random-access memory (RAM), CD-ROMs, magnetic tapes, floppy disks, and optical data storage. The computer readable recording medium can also be distributed over network coupled computer systems so that the computer readable code may be stored and executed in a distributed fashion.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of operating an ultrasonic diagnostic apparatus, the method comprising:
   displaying an ultrasonic image in a first region of a display unit;
   selecting a region of interest (ROI) in the ultrasonic image;
   displaying a first scan conversion image and a second scan conversion image in a second region, wherein the first scan conversion image is generated by enlarging or reducing an image corresponding to the selected ROI at a first magnification and the second scan conversion image is generated by enlarging or reducing the image corresponding to the selected ROI at a second magnification; and
   acquiring a first measurement value of the ROI on the basis of the first scan conversion image, acquiring a second measurement value of the ROI on the basis of the second scan conversion image, and acquiring a third value calculated on the basis of the first and second measurement values,
   wherein resolution of the scan conversion image is equal to or higher than resolution of the ultrasonic image.

2. The method of claim 1, wherein the selecting of an ROI comprises selecting the ROI on the basis of a user input, wherein the user input comprises at least one of an input for selecting a certain region in the ultrasonic image, an input of a coordinate value of the certain region, and an input for selecting a specific object included in the ultrasonic image.

3. The method of claim 1, wherein the acquiring of the first measurement value and the second measurement value comprises acquiring at least one measurement value of a distance, an area, an angle, and a volume of an object of interest included in the ROI.

4. The method of claim 1, further comprising displaying the first measurement value and the second measurement value.

5. The method of claim 1, wherein,
   the displaying of the first scan conversion image and the second scan conversion image comprises displaying the first scan conversion image with the first magnification and displaying the second scan conversion image with the second magnification.

6. The method of claim 1, wherein the displaying of the first scan conversion image and the second scan conversion image comprises:
   detecting an edge of an object of interest included in the ROI on the basis of image data corresponding to the ROI; and
   displaying the detected edge of the object of interest on at least one of the first scan conversion image and the second scan conversion image.

7. The method of claim 6, wherein the detecting of an edge comprises detecting the edge of the object of interest on a basis of first and second edge detection techniques.

8. The method of claim 7, wherein the displaying of the first scan conversion image and the second scan conversion image comprises displaying a first edge detection image, in which a first edge detected by the first edge detection technique is displayed on at least one of the first scan conversion image and the second scan conversion image, and a second edge detection image in which a second edge detected by the second edge detection technique is displayed on at least one of the first scan conversion image and the second scan conversion image.

9. An ultrasonic diagnostic apparatus comprising:
   a user input interface that receives a user input for selecting a region of interest (ROI) in an ultrasonic image;
   an image processor that generates a first scan conversion image by enlarging or reducing an image corresponding to the ROI at a first magnification and generates a second scan conversion image by enlarging or reducing the image corresponding to the ROI at a second magnification;
   a display that displays the first scan conversion image and the second scan conversion image; and
   a controller that acquires a first measurement value of an object of interest in the ROI on the basis of the first scan conversion image, acquires a second measurement value of the object of interest in the ROI on the basis of the second scan conversion image, and acquires a third value calculated on the basis of the first and second measurement values;
   wherein a resolution of the scan-converted image is equal to or higher than a resolution of the ultrasonic image.

10. The ultrasonic diagnostic apparatus of claim 9, wherein the user input interface receives at least one of an input for selecting a certain region in the ultrasonic image, an input of a coordinate value of the certain region, and an input for selecting a specific object included in the ultrasonic image.

11. The ultrasonic diagnostic apparatus of claim 9, wherein the controller acquires at least one measurement value of a distance, an area, an angle, and a volume of the object of interest included in the ROI.

12. The ultrasonic diagnostic apparatus of claim 9, wherein the display unit displays the first measurement value and the second measurement value.

13. The ultrasonic diagnostic apparatus of claim 9, wherein,
the display unit displays the first scan conversion image with the first magnification and the second scan conversion image with the second magnification.

14. The ultrasonic diagnostic apparatus of claim 9, further comprising an edge detector that detects an edge of the object of interest included in the ROI on the basis of image data corresponding to the ROI,
wherein at least one of the first scan conversion image and the second scan conversion image includes the detected edge.

15. The ultrasonic diagnostic apparatus of claim 14, wherein the edge detector detects the edge of the object of interest on a basis of first and second edge detection techniques.

16. The ultrasonic diagnostic apparatus of claim 15, wherein the display displays a first edge detection image, in which a first edge detected by the first edge detection technique is displayed on at least one of the first scan conversion image and the second scan conversion image, and a second edge detection image in which a second edge detected by the second edge detection technique is displayed on at least one of the first scan conversion image and the second scan conversion image.

17. The method of claim 1, wherein the third value includes at least one of an average value, variance, and standard deviation of the first measurement value and second measurement value.

\* \* \* \* \*